(12) United States Patent
Sugiyama

(10) Patent No.: US 8,789,405 B2
(45) Date of Patent: Jul. 29, 2014

(54) CALIBRATION METHOD IN MEASUREMENT OF HEMOGLOBIN A1C

(75) Inventor: Koji Sugiyama, Kyoto (JP)

(73) Assignee: ARKRAY, Inc., Kyoto-shi (JP)

( * ) Notice: Subject to any disclaimer, the term of this patent is extended or adjusted under 35 U.S.C. 154(b) by 25 days.

(21) Appl. No.: 13/284,132

(22) Filed: Oct. 28, 2011

(65) Prior Publication Data

US 2012/0103054 A1    May 3, 2012

(30) Foreign Application Priority Data

Oct. 28, 2010    (JP) ................. 2010-241827

(51) Int. Cl.
*G01N 30/00* (2006.01)
*G01N 30/88* (2006.01)
*G01N 30/86* (2006.01)
*G01N 27/447* (2006.01)
*G01N 33/96* (2006.01)
*G01N 33/72* (2006.01)
*G01N 30/04* (2006.01)

(52) U.S. Cl.
CPC ............ *G01N 30/88* (2013.01); *G01N 30/8665* (2013.01); *G01N 30/86* (2013.01); *G01N 2030/8822* (2013.01); *G01N 27/447* (2013.01); *G01N 2030/042* (2013.01); *G01N 33/96* (2013.01); *G01N 33/723* (2013.01)
USPC .............................................. 73/1.02

(58) Field of Classification Search
None
See application file for complete search history.

(56) References Cited

U.S. PATENT DOCUMENTS

| | | | |
|---|---|---|---|
| 2003/0068822 | A1 | 4/2003 | Jacobs et al. |
| 2009/0275140 | A1 * | 11/2009 | Pistorino et al. ............... 436/15 |
| 2010/0006436 | A1 | 1/2010 | Oishi et al. |
| 2010/0155242 | A1 | 6/2010 | Nakayama et al. |
| 2010/0168535 | A1 | 7/2010 | Robinson et al. |
| 2010/0187110 | A1 | 7/2010 | Tanaka et al. |

FOREIGN PATENT DOCUMENTS

| | | |
|---|---|---|
| CN | 101501484 A | 8/2009 |
| JP | H04-190158 A | 7/1992 |
| JP | H06-324027 A | 11/1994 |
| JP | 2003-344417 A | 12/2003 |
| JP | 2009-109231 A | 5/2009 |
| WO | 2008/029684 A1 | 3/2008 |
| WO | 2008/029685 A1 | 3/2008 |

OTHER PUBLICATIONS

Shima et al., "An Interim Report of the Committee on an Interlaboratory Standardization of HbA1c Determination", Journal of the Japan Diabetes Society, vol. 37, No. 3, p. 233-243, 1994 with its English Abstract.

Takei et al., "Japanese Guideline for reporting HbA1c results reported in IFCC units and JDS units", Journal of Japan Society of Clinical Chemistry, vol. 37, No. 4, p. 393-409, 2008 with its English Abstract.

(Continued)

*Primary Examiner* — Robert R Raevis
(74) *Attorney, Agent, or Firm* — Fox Rothschild LLP

(57) ABSTRACT

A calibration method that enables calibration easily in a short time in a measurement of hemoglobin A1c by use of a separation analysis is provided. In a measurement of a hemoglobin A1c amount by use of a separation analysis, a one-point calibration using a single calibration standard is performed to obtain calibration data to be used for correcting a measured value.

10 Claims, 1 Drawing Sheet

(56) References Cited

OTHER PUBLICATIONS

Kuramura et al., "Fundamental evaluation of HbA1c measurement using ADAMS-A1c HA-8170", Journal of Medicine and Pharmaceutical Science, vol. 58, No. 2, p. 355-361, 2007.

Murakami et al., "Development of Tosoh Automated Glycohennoglobin Analyzer HLC-723G8", TOSOH Research & Technology Review, vol. 50, p. 69-72, 2006.

Catalog of Tosoh Corporation automated glycohemoglobin analyzer HLC-723 G8, 2005.

* cited by examiner

CALIBRATION METHOD IN MEASUREMENT OF HEMOGLOBIN A1C

INCORPORATION BY REFERENCE

The present application claims priority under 35 U.S.C. §119 to Japanese Patent Application No. 2010-241827 filed Oct. 28, 2010, the content of which being incorporated herein by reference in its entirety.

BACKGROUND OF THE INVENTION

1. Field of the Invention

The present invention relates to a calibration method in a measurement of hemoglobin A1c by use of a separation analysis.

2. Description of Related Art

In the field of diabetes treatment, a special emphasis has been placed on a strict control of blood glucose values for the purpose of preventing critical complications. In particular, accuracy and precision of hemoglobin A1c (hereinafter, also referred to as "HbA1c") level as an index in the control of blood glucose values constitutes an important factor to be monitored that can even influence the quality of diabetes treatment.

There have been considerable variations for HbA1c measuring apparatuses depending on manufactures and facilities, and there have been problems in the accuracy in HbA1c values. However, there has been a remarkable improvement in solving these problems as a result of standardization in the method of measuring the HbA1c (see 'An Interim Report of the Committee on an Interlaboratory Standardization of HbA1c Determination' Journal of the Japan Diabetes Society, Vol. 37, No. 3, p. 233-243, 1994 for example). Furthermore, and more recently, a guideline was established for standardizing the HbA1c value that has been expressed differently among countries. Thus, the role of system configuration in the HbA1c measurement has become more important (see 'Japanese Guideline for reporting HbA1c results reported in IFCC units and JDS units' Journal of Japan Society of Clinical Chemistry, Vol. 37, No. 4, p. 393-409, 2008 for example).

For a measurement of an HbA1c amount, for example, a separation analysis, an affinity measurement, an immunization measurement, an enzyme measurement and the like have been used. Apparatuses and reagents to be used exclusively for HbA1c measurements have also come into commercial use. Among them, in the field of diabetes treatment, utility of HbA1c measurement by use of the separation analysis has been extensively evaluated. For this reason, for example, apparatuses employing the separation analysis such as high pressure liquid chromatography (HPLC) have come into commercial use. Examples thereof include ADAMS A1c HA-8170 (trade name, supplied by ARKRAY, Inc. (see 'Fundamental evaluation of HbA1c measurement using ADAMS-A1c HA-8170' Journal of Medicine and Pharmaceutical Science, Vol. 58, No. 2, p. 355-361, 2007 for example)) and HLC-723G8 (trade name, supplied by Tosoh Corporation (see 'Development of Tosoh Automated Glycohemoglobin Analyzer HLC-723G8' TOSOH Research & Technology Review for example)). Each of the apparatuses is packaged with a system calibration function due to the above-mentioned reason. For the calibration method, a calibration method is employed using two calibration standards with different HbA1c values to establish two calibration data points (two-point calibration method) (see 'Catalog of Tosoh Automated Glycohemoglobin Analyzer HLC-723G8' (Tosoh Corporation) for example)).

Furthermore, separation analysis methods other than the HPLC method can be used. For example, HbA1c measurement technology using capillary electrophoresis is currently under development (see WO 2008/029684 and WO 2008/029685 for example).

SUMMARY OF THE INVENTION

From the viewpoint of presenting rapidly to a patient a measurement result, there has been a requirement for performing a measurement easily in a short time. Therefore, the present invention provides a new calibration method enabling a calibration more easily in a short time during the measurement of hemoglobin A1c levels by use of a separation analysis.

The present invention relates to a calibration method including performing a one-point calibration by using one calibration standard during the measurement of hemoglobin A1c levels by use of a separation analysis. The obtained calibration data is used for correcting a measured value of hemoglobin A1c.

In a typical hemoglobin A1c measuring apparatus based on a separation analysis, calibration is performed by establishing at least two different calibration data points. According to the present invention, the calibration is performed by establishing only one calibration point. Thus, the present invention enables calibration easily in a short time.

DETAILED DESCRIPTION OF THE INVENTION

Figure 1:
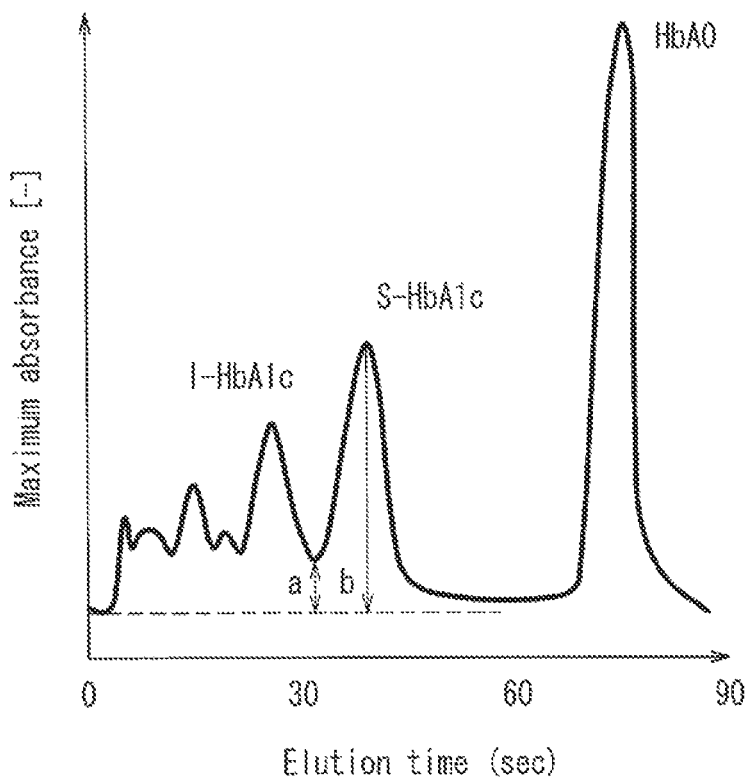
FIG. 1 is a conceptual diagram for explaining a method for computation of a separation index.

The present invention is based on a finding that in a measurement of HbA1c levels by use of a separation analysis, a one-point calibration using only a single calibration standard can provide an HbA1c value of substantially the same accuracy as in the case of calibrating using at least two calibration standards with different HbA1c values.

In general, in any measurement of HbA1c levels by use of a separation analysis (measuring apparatus), a calibration method is employed using at least two calibration standards of different HbA1c values to establish two calibration data points. This is based on a determination that in a case of creating a calibration curve to be used for calibration using only a single calibration standard, the calibration curve does not pass through a zero point. As a result, sufficient precision cannot be obtained without calibrating by using at least two calibration standards of different HbA1c values. A specific example of measuring apparatus is ADAMS A1cHA-8170 (trade name, supplied by ARKRAY, Inc.), which performs calibration of a measuring apparatus by use of two different calibration standards, i.e., HbA1c indicated values of about 35 mmol/mol and about 90 mmol/mol. Further examples of factors for inhibiting the curve to pass through the zero point are considered to include existence of minor components other than the stable HbA1c (for example, labile HbA1c fraction, carbamylated Hb fraction, acetylated Hb fraction and the like) that has an elution time substantially similar to that of the stable HbA1c to be measured. This is a problem characteristic to the respective apparatuses. Due to these reasons, it has been considered in this field that in a measurement of HbA1c by use of a separation analysis, a calibration method using at least two calibration standards of different HbA1c values to obtain different calibration data points is essential. There has not been any discussion even on possibility of calibration using calibration standards for providing less than two calibration standards points.

On the other hand, from the viewpoint of shortening the measurement time, using a less number of calibration standards with a less number of calibration data points is preferred. Taking this into consideration, the inventor studied the number of calibration data points and the measurement precision so as to find out a relationship between the bias of the calibration curve and the separation performance of the stable HbA1c (s-HbA1c) in the separation analysis. Specifically, it was found that the bias of the calibration curve relies on the mutual interaction between the s-HbA1c fraction and an Hb minor component other than s-HbA1c that is separated before or after the s-HbA1c fraction. Namely, the present invention is based on a finding that a calibration by a one-point calibration method is applicable by eliminating influence of Hb minor component other than the s-HbA1c, which is contrary to the conventional denial against the possibility of using such a one-point calibration method. Further, the present invention is based on a finding that a calibration by a one-point calibration method is applicable by performing a separation analysis under a condition where a separation index mentioned below would be within a predetermined range.

According to the present invention, in a measurement of an HbA1c amount by use of a separation analysis, calibration is performed as a one-point calibration method using only one calibration standard. Thus, for example the time required for the calibration can be shortened, and furthermore, the time for measuring the HbA1c levels can be shortened. Lastly according to the present invention, since only one calibration standard is necessary for calibration, the cost performance in calibration and/or measurement of the HbA1c amount can be improved.

In the present Specification, "calibration data" are used to correct a measured value in a measurement of an HbA1c amount by use of a separation analysis. The data can be obtained by performing a one-point calibration using only one calibration standard. An example of the calibration data is a calibration curve. A preferred calibration curve is created by using a measured value of HbA1c amount of one calibration standard measured by use of a separation analysis and an indicated value of the calibration data point obtained for the calibration sample.

In the present Specification, "measured value" denotes a value of an amount of HbA1c before correction with the calibration data obtained by the calibration method of the present invention. The value includes, for example, an actual measured value obtained by measuring a sample by use of the separation analysis. In the present Specification, "correction of measured value" denotes correcting a measured value by using the above-mentioned calibration data. It includes, for example, making the measured value more accurate (i.e., the measured HbA1c amount) by using the above-mentioned calibration data.

In the present Specification, "one-point calibration" denotes performing a calibration by using one calibration data point obtained by using only one calibration standard with a known level of HbA1c. Preferably, it includes creating a calibration curve that links an origin and single calibration data point obtained by using the one calibration standard containing HbA1c. More preferably, it includes measuring an HbA1c amount in one calibration standard by use of the separation analysis and creating a calibration curve by using the thus obtained measured value and the HbA1c amount (indicated value) described on the used calibration standard.

In the present Specification, "hemoglobin A1c (HbA1c)" denotes a structure in which a glucose binds to a β-chain N-terminal of hemoglobin, preferably it denotes a stable HbA1c (s-HbA1c).

In the present Specification, "hemoglobin A1c amount (HbA1c amount)" denotes a concentration of HbA1c in a sample or blood. From a practical viewpoint, preferably it denotes an HbA1c value. In the present Specification, "HbA1c value" denotes a ratio of HbA1c to hemoglobin in a sample or blood (HbA1c concentration/hemoglobin concentration), and the unit is mmol/mol or %.

In the present Specification, "separation analysis" denotes a method for performing an analysis while separating respective analytes included in a sample, and the examples include liquid chromatography, capillary electrophoresis, capillary electric chromatography, and the like. Examples of liquid chromatography include cation exchange chromatography, anion exchange chromatography, partition chromatography, reversed-phase partition chromatography, affinity chromatography, gel filtration chromatography and the like. Examples of capillary electrophoresis include capillary zone electrophoresis, capillary isoelectric point electrophoresis, capillary conductive chromatography, capillary isotachophoresis, capillary gel electrophoresis and the like.

[Calibration Method]

The present invention relates to a calibration method including performing a one-point calibration method using one calibration standard so as to obtain calibration data to be used for correction of a measured value during the measurement of an HbA1c amount by use of a separation analysis.

It is preferable that the calibration data are provided as a calibration curve. It is also preferable that the calibration curve is created by using a measured value of an HbA1c amount of a calibration standard measured by use of the separation analysis and an indicated value of the calibration standard. It is more preferable that the calibration curve is created by using a substance whose HbA1c value is zero and a single calibration data point from the single calibration standard. It is further preferable that multiple measurements are taken for the calibration data point (i.e., single point), which is then subjected to a linear regression with the zero point on the calibration curve by the least-squares method or the like, thereby obtaining a straight calibration line. Alternatively, the calibration line can be created by calculating averages of the values obtained by the multiple measurements of the calibration standard and by linking the averages with a straight line.

From a viewpoint of improving the calibration precision, a preferred embodiment of the calibration method of the present invention is to perform a separation analysis of a calibration standard where the separation index as defined below is within a predetermined range. Preferably, it is to perform a separation analysis where the separation index is not less than 0 and not more than 0.2. Further preferably, the separation index is more than 0 and not more than 0.1; still preferably, more than 0 and not more than 0.06. The separation index is obtained by using the equation below, using a bottom height (a) between the s-HbA1c fraction and a fraction separated before/after the s-HbA1c fraction, and a peak height (b) of the s-HbA1c fraction, in a separation pattern obtained by the separation analysis.

$$\text{Separation index} = \{\text{bottom height }(a)\text{ between s-HbA1c fraction and a fraction separated before/after s-HbA1c fraction}\}/\{\text{peak height }(b)\text{ of s-HbA1c fraction}\}$$

It is preferable that the bottom height (a) is a bottom height between the fraction separated while partly overlapped with the fraction of the s-HbA1c as the measurement target and the s-HbA1c fraction. In a case where the s-HbA1c fraction and the fraction separated before the s-HbA1c fraction are partly overlapped with each other, the bottom height between the s-HbA1c fraction and the fraction separated before the s-HbA1c fraction is preferred. In a case where the s-HbA1c fraction and the fraction separated after the s-HbA1c fraction are partly overlapped with each other, the bottom height between the s-HbA1c fraction and the fraction separated after the s-HbA1c fraction is preferred. In a case where the s-HbA1c fraction is overlapped with both the fractions separated before and after the s-HbA1c fraction, it is preferable that the separation index is calculated by using respectively the bottom height between the s-HbA1c fraction and the fraction separated before the s-HbA1c fraction and also the bottom height between the s-HbA1c fraction and the fraction separated after the s-HbA1c fraction.

The bottom height (a) and the peak height (b) of the s-HbA1c fraction can be measured as shown in FIG. 1 for example. FIG. 1 is a graph showing an example of a separation pattern obtained by measurement of HbA1c amount by use of liquid chromatography. In the example shown in FIG. 1, the s-HbA1c fraction as the analyte is partly overlapped with a labile HbA1c (l-HbA1c) fraction separated before the s-HbA1c fraction. Therefore, in the example of FIG. 1, the bottom height (a) is set as a bottom height between the s-HbA1c fraction and the l-HbA1c fraction separated before the s-HbA1c fraction. The bottom height (a) can be computed by calculating the difference between the base absorbance and the lowest absorbance between the l-HbA1c fraction and the s-HbA1c fraction. The peak height (b) of the s-HbA1c fraction can be computed by calculating the difference between the base line absorbance and the highest absorbance (peak absorbance) of the s-HbA1c fraction.

In a case of performing a separation analysis by use of the liquid chromatography, the separation precision can be improved and a separation pattern having the above-mentioned separation precision can be obtained by for example decreasing the column diameter, increasing the length of the column, decreasing the fluid velocity, and decreasing the gel particle diameter. In a case of performing a separation analysis by use of the capillary electrophoresis, the separation precision can be improved by for example increasing the length of the capillary.

It is preferable that the HbA1c value (HbA1c concentration/Hb concentration) of the calibration standard is 14 to 400 mmol/mol (IFCC value) for example. From the viewpoint of improving the calibration precision and/or the measurement precision, it is more preferable that the HbA1c value is 14 to 190 mmol/mol, and further preferably, 25 to 150 mmol/mol. The HbA1c value of the calibration standard is preferably 3 to 40% for example. From the viewpoint of improving the calibration precision and/or the measurement precision, it is more preferable that the HbA1c value is 3 to 20%, and further preferably, 4 to 16%.

A measurement of the HbA1c value can be performed by measuring the absorbance with a wavelength corresponding to HbA1c. An example of the wavelength corresponding to HbA1c is a wavelength in a range of 415 to 430 nm.

[Method for Measuring HbA1c Amount]

In another aspect, the present invention relates to a method for measuring an HbA1c amount, and the method includes measuring an HbA1c amount of a sample by use of a separation analysis and correcting a hemoglobin A1c amount obtained by the measurement with calibration data obtained by the above-mentioned calibration method of the present invention. According to the method for measuring HbA1c amount of the present invention, since correction of the measured value of the HbA1c amount is performed by using the calibration data obtained by the calibration method of the present invention, for example, the time necessary for the calibration can be shortened and thus the measurement time can be shortened.

The method for measuring the HbA1c amount of the present invention may include measurement of absorbance at a wavelength corresponding to HbA1c.

[Analyzer]

In a further aspect, the present invention relates to an analyzer comprising a measuring section that separates a component including HbA1c in a sample by use of a separation analysis and measures the separated component, a controlling section that performs one-point calibration with the one calibration standard at the measuring section so as to obtain calibration data to be used for correction of the measured value, and a recording section that records the calibration data obtained at the controlling section. The controlling section relates to an analyzer that corrects, with the calibration data the hemoglobin A1c amount of the sample obtained at the measuring section. According to the analyzer of the present invention, since the measured value of the hemoglobin A1c amount is corrected with the calibration data obtained by the calibration method of the present invention, for example, the time necessary for the calibration can be shortened, and thus the measurement time can be shortened. Furthermore, since calibration data obtained by a one-point calibration is used for the calibration data, the analysis precision can be improved.

It is preferable that the controlling section creates a calibration curve by using the measured value of the hemoglobin HbA1c amount of the calibration standard measured by use of the separation analysis and the indicated value of HbA1c calibration standard, and uses the thus obtained calibration curve as the calibration data.

It is preferable that the measuring section has a separation device that separates a component including HbA1c in a sample.

It is preferable that the analyzer of the present invention has for example a mode to be subjected to a one-point calibration by use of the calibration method of the present invention, for the purpose of obtaining calibration data.

[Program]

In a further aspect, the present invention relates to a non-transitory computer-readable recording medium storing a calibration program to make a computer execute a calibration by the above-mentioned calibration method of the present invention. In a further aspect, the present invention relates to a non-transitory computer-readable recording medium storing an analysis program to make a computer execute a process so that the computer controls an analyzer that measures the HbA1c amount by separating a component including HbA1c in a sample by use of a separation analysis, and the program makes the computer execute a process of obtaining calibration data through the above-mentioned calibration method of the present invention, and a process of correcting the hemoglobin A1c amount obtained through the measurement, by use of the calibration data. More specifically, the analysis program relates to an analysis program to make a computer execute a process of creating a calibration curve by using a measured value of an HbA1c amount of one kind of calibration standard measured by use of the above-mentioned separation analysis and an indicated value of the calibration standard.

It is preferable that the analysis program makes further the computer execute a process of correcting a measurement data obtained at the analyzer, by use of the calibration curve.

[Calibration Kit]

In a further aspect, the present invention relates to a calibration kit that is used in the calibration method of the present invention and that includes one calibration standard for establishing the one-point calibration data. The calibration kit of the present invention can be used for the calibration method of the present invention.

It is preferable that the calibration kit of the present invention includes an attached document describing, as the HbA1c amount of the calibration standard, an HbA1c value or both the HbA1c concentration and an Hb concentration, for example. It is preferable that the document includes description of a method of creating the above-mentioned data or the like by using the calibration standard. Thereby, the calibration method of the present invention can be performed easily.

Hereinafter, an embodiment of the present invention will be described specifically with reference to the attached drawings. It should be noted however that the description below refers to only one example, and that the present invention is not limited to this example.

Figure 2:
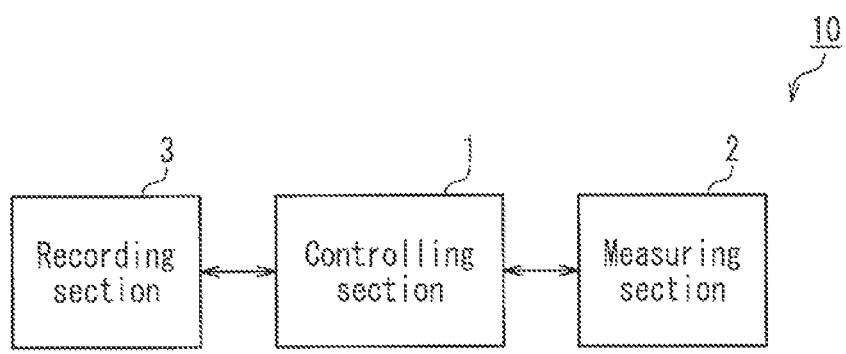
FIG. 2 is a functional block diagram showing a configuration example of analyzer in an embodiment.

FIG. 2 is a functional block diagram showing a configuration example of an analyzer according to an embodiment of the present invention. An analyzer 10 shown in FIG. 2 is an analyzer employing a separation analysis, and it separates a component included in a sample so as to quantify the separated component. The analyzer 10 has a recording section 3, a controlling section 1, and a measuring section 2. The measuring section 2 separates a component including HbA1c in a sample by use of a separation analysis and measures the thus separated component. The controlling section 1 calculates an HbA1c amount by using the measurement data obtained at the measuring section 2 and calibration data. The recording section 3 records the calibration data.

The analyzer 10 as shown in FIG. 2 obtains calibration data by performing a one-point calibration using only one calibration standard at the controlling section 1. Specifically, the controlling section 1 creates a calibration curve by using a measured value of an HbA1c amount in the calibration standard measured by use of the separation analysis and an indicated value of the calibration standard used for the measurement, and uses the thus obtained calibration curve as the calibration data. Since the calibration data are obtained through the one-point calibration method in this manner, for example, the time for calibration can be decreased remarkably and the calibration data can be obtained in a simple manner.

The calibration data are used to correct the measurement data obtained at the measuring section 2. By computing the HbA1c amount by using the calibration data and the measurement data in this manner, a further precise HbA1c amount can be obtained.

It is preferable that the separation analysis of the calibration standard is performed under a condition where the above-mentioned separation index (=(a)/(b)) defined by the peak height (b) of s-HbA1c faction and the bottom height (a) between the s-HbA1c fraction and a fraction separated before or after the s-HbA1c faction in a separation pattern obtained by the separation analysis is within a predetermined range. It is preferable that the separation index is for example not less than 0 and not more than 0.2; more preferably, more than 0 and not more than 0.2; further preferably, more than 0 and not more than 0.1; and still further preferably, more than 0 and not more than 0.06.

The function of the controlling section 1 shown in FIG. 2 is provided as a result of execution of a predetermined program by a microprocessor that is built in either a measuring apparatus or by a general purpose computer such as a personal computer having CPU. The recording section 3 can be composed of a recording device such as HDD or memory accessible from a processor of a computer. The analyzer 10 may be formed by integrating the controlling section 1, the measuring section 2 and the recording section 3. Alternatively, it may be formed by connecting a general purpose computer to an independent measuring section 2. Further, a program for functioning the computer as the above-mentioned controlling section 1 or a recording medium on which the program has been recorded is also included in the embodiment of the present invention. An analyzing method executed by the computer is also one aspect of the present invention. Here, the recording media do not include non-transitory media such as a signal itself.

Hereinafter, the present invention will be described more specifically by citing EXAMPLES and REFERENCES, though the present invention is not limited to EXAMPLES below.

EXAMPLES

First, under the measurement condition as indicated in Table 1 below, a measurement of HbA1c was performed by using the following two calibration standards, and a calibration curve was created based on the obtained two calibration points.

[Two Calibration Standards of Different HbA1c Values]

Calibration Standards dedicated to ADAMS A1c HA-8160 level 1 (HbA1c value: 35 mmol/mol) and Level 2 (HbA1c value: 95 mmol/mol; supplied by ARKRAY, Inc.)

For the capillary tube, five types of capillary tubes different from each other in the capillary length were prepared. Each of the capillary tubes (inner diameter: 50 μm) was made of molten silica having an inner wall having a cathode layer formed by fixing by a covalent bond a silylation agent having a sulfone group.

For providing a running buffer, an aqueous solution of arginine acid containing 100 mM malic acid was prepared, to which chondroitin sulfuric acid was added up to a concentration of 0.5 wt % (pH 5.5).

Purified water was passed through each of the capillary tubes for 20 minutes at a pressure of 0.1 MPa (1000 mbar), the capillary tube was washed, and then the running buffer (pH 5.5) was passed through at a pressure of 0.1 MPa (1000 mbar) so as to fill the capillary tube with the running buffer. In this state, the above-mentioned calibration standard was injected from the anode side of the capillary tube, and subsequently the both ends of the capillary tube were applied with a voltage of 10 kV for the purpose of electrophoresis, thereby measuring absorbance at 415 nm (n=3).

An area corresponding to the s-HbA1c fraction and an area corresponding to the total hemoglobin were computed from the obtained separation pattern, which were used to compute the ratio of the s-HbA1c to the total hemoglobin. A calibration curve was created by setting an HbA1c value (mmol/mol) described for each calibration standard to the Y-axis, and the obtained HbA1c value (area corresponding to s-HbA1c/area corresponding to total hemoglobin) of each of the obtained calibration data points to the X-axis. The y-intercept of the obtained calibration curve is shown as a bias for a two-point calibration in Table 1 below.

Furthermore, the bottom height (a) between the s-HbA1c fraction and a l-HbA1c fraction separated before the s-HbA1c fraction and also the peak height (b) of the s-HbA1c fraction were measured from the obtained separation pattern, from which a separation index was computed by use of the equation below. The results are shown in Table 1 below.

Separation index={bottom height (a) between s-HbA1c fraction and l-HbA1c fraction}/{peak height (b) of s-HbA1c fraction}

TABLE 1

|  | Condition A | Condition B | Condition C | Condition D | Condition E |
|---|---|---|---|---|---|
| Capillary length (mm) | 30 | 60 | 90 | 120 | 150 |
| Separation index | 0.40 | 0.28 | 0.20 | 0.18 | 0.17 |
| Bias at two-point calibration (mmol/mol) | 3.9 | 2.2 | 0.08 | 0.06 | 0.05 |

It is evident from Table 1 that the bias at the two-point calibration relies on the separation index, and that the bias at two-point calibration was not more than 0.1 mmol/mol when the separation index was not more than 0.20.

Next, a measurement of an HbA1c value was performed by using the following calibration standard for one-point calibration, and the thus obtained calibration point (only one point) and the origin were linked to create a calibration curve (one-point calibration). Next, a measurement of the HbA1c amount of the sample was performed, so that the HbA1c value of the sample was obtained by using the calibration curve created by use of only the single calibration standard for one-point calibration. For the sample, certified reference material for measurement of HbA1c JCCRM411-2 (5 concentrate levels, traceability to IFCC reference system supplied by Reference Material Institute for Clinical Chemistry Standards) were used.

[Calibration Standard for One-Point Calibration]

Calibration standard dedicated to ADAMS A1c HbA1c-8160 level 2 (HbA1c value: 95 mmol/mol) (supplied by ARKRAY, Inc.)

Measurements of HbA1c amount for the calibration standard and the sample were performed under the substantially same condition as mentioned above.

An area corresponding to the s-HbA1c and an area corresponding to the total hemoglobin were computed from the separation pattern of the calibration standard, which were used to compute the ratio of the s-HbA1c (HbA1c value) to the total hemoglobin. Next, a calibration curve (a calibration curve by a one-point calibration) was created by using the HbA1c value described on the calibration standard and the obtained HbA1c value of the calibration data point, so that the y-intercept would be 0.

Next, HbA1c value (=(area corresponding to s-HbA1c)/(area corresponding to total hemoglobin)) was computed from the separation pattern of each of the samples. The obtained HbA1c value was calibrated by using the calibration curve provided by the one-point calibration. The results are indicated as the measurement results in the Table 2 below. In Table 2 below, a difference denotes a difference between the indicated value of JCCRM411-2 and the measured value (HbA1c value), i.e., (measurement result (HbA1c value)−(indicated value of JCCRM411-2)).

TABLE 2

|  | 1 | 2 | 3 | 4 | 5 |
|---|---|---|---|---|---|
| Separation index: 0.40 | | | | | |
| Indicated value of JCCRM411-2 (mmol/mol) | 30.6 | 37.1 | 54.9 | 78.6 | 104.2 |
| Measurement result (mmol/mol) | 27.7 | 34.5 | 52.9 | 78.1 | 104.1 |
| Difference (ΔA1c) | −2.9 | −2.6 | −2.0 | −0.5 | −0.1 |
| Separation index: 0.28 | | | | | |
| Indicated value of JCCRM411-2 (mmol/mol) | 30.6 | 37.1 | 54.9 | 78.6 | 104.2 |
| Measurement result (mmol/mol) | 28.9 | 35.6 | 53.7 | 78.4 | 104.0 |
| Difference (ΔA1c) | −1.7 | −1.5 | −1.2 | −0.2 | −0.2 |
| Separation index: 0.20 | | | | | |
| Indicated value of JCCRM411-2 (mmol/mol) | 30.6 | 37.1 | 54.9 | 78.6 | 104.2 |
| Measurement result (mmol/mol) | 29.8 | 36.5 | 54.3 | 78.7 | 103.9 |
| Difference (ΔA1c) | −0.8 | −0.6 | −0.6 | 0.1 | −0.3 |
| Separation index: 0.06 | | | | | |
| Indicated value of JCCRM411-2 (mmol/mol) | 30.6 | 37.1 | 54.9 | 78.6 | 104.2 |
| Measurement result (mmol/mol) | 30.0 | 36.6 | 54.4 | 78.8 | 103.9 |
| Difference (ΔA1c) | −0.6 | −0.5 | −0.5 | 0.2 | −0.3 |
| Separation index: 0.05 | | | | | |
| Indicated value of JCCRM411-2 (mmol/mol) | 30.6 | 37.1 | 54.9 | 78.6 | 104.2 |
| Measurement result (mmol/mol) | 30.1 | 36.7 | 54.5 | 78.8 | 103.9 |
| Difference (ΔA1c) | −0.5 | −0.4 | −0.4 | 0.2 | −0.3 |

As indicated in the above Table 2, with the decrease in the separation index, the difference between the indicated value and the measured value calibrated by the one-point calibration was reduced. In particular, when the separation index was 0.20 or less, the difference was 1 mmol/mol or less, which is a substantially nonsignificant level.

Industrial Applicability

The present invention can be applied favorably in various fields such as medicine, a clinical test, treatment and prevention of diabetes and the like.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A calibration method comprising performing a one-point calibration by using only a single calibration standard in a measurement of a hemoglobin A1c amount by use of a separation analysis so as to obtain calibration data to be used for correction of a measured value,
   wherein in a separation pattern of the calibration standard obtained by the separation analysis, a separation index defined by a bottom height (a) between a stable hemoglobin A1c fraction and a fraction separated before or after the stable hemoglobin A1c fraction and a peak height (b) of the stable hemoglobin A1c fraction is not less than 0 and not more than 0.2:

Separation index={bottom height (a) between stable hemoglobin A1c fraction and a fraction separated before/after thereof}/{peak height (b) of stable hemoglobin A1c fraction}.

2. The calibration method according to claim 1, wherein the calibration data are provided as a calibration line, and the method comprises creating the calibration line by using the measured value of the hemoglobin A1c amount of the calibration standard measured by use of the separation analysis and an indicated value of the calibration standard.

3. The calibration method according to claim 1, wherein the calibration standard has a hemoglobin A1c value (hemoglobin A1c concentration/hemoglobin concentration) in a range of 14 to 400 mmol/mol (IFCC value).

4. The calibration method according to claim 1, wherein the separation analysis is selected from the group consisting of high performance liquid chromatography, capillary electrophoresis, and capillary electric chromatography.

5. The calibration method according to claim 1, wherein a high performance liquid chromatography is selected from the group consisting of cation exchange chromatography, anion exchange chromatography, partition chromatography, reversed-phase partition chromatography, affinity chromatography, and gel filtration chromatography.

6. The calibration method according, to claim 1. wherein a capillary electrophoresis is selected from the group consisting of capillary zone electrophoresis, capillary isoelectric point electrophoresis, capillary electrokinetic chromatography, capillary isotachophoresis, and capillary gel electrophoresis.

7. A method for measuring a hemoglobin A1c amount, comprising:
    measuring a hemoglobin A1c amount in a sample by use of a separation analysis; and
    correcting the hemoglobin A1c amount obtained by the measurement, by using calibration data obtained by the calibration method according to claim 1.

8. A non-transitory computer-readable recording medium storing a calibration program for making a computer execute a calibration process by the calibration method according to claim 1.

9. A non-transitory computer-readable recording medium storing an analysis program that makes a computer execute a process of controlling an analyzer that separates a component including hemoglobin A1c in a sample by use of a separation analysis and that measures the hemoglobin A1c amount,
    the analysis program makes the computer execute a process of obtaining calibration data by the calibration method according to claim 1 and a process of correcting the hemoglobin A1c amount obtained by the measurement, by using the calibration data.

10. An analyzer comprising a measuring section that separates a component including hemoglobin A1c in a sample by use of a separation analysis and that measures the separated component;
    a controlling section that performs a one-point calibration by using only a single calibration standard at a measuring portion so as to obtain calibration data to be used for correcting a measured value; and
    a recording section that records the calibration data obtained at the controlling section,
    the controlling section corrects the hemoglobin A1c measurement of the sample obtained at the measuring section, by using the calibration data.

* * * * *